(12) United States Patent
Comely et al.

(10) Patent No.: US 7,893,258 B2
(45) Date of Patent: Feb. 22, 2011

(54) PREPARATION OF DELMOPINOL

(75) Inventors: Alexander Comely, Barcelona (ES);
Llorenç Rafecas Jane, Llorenç del Penedes (ES); Nicolas Tesson, Barcelona (ES); Antoni Riera Escale, Barcelona (ES)

(73) Assignee: Sinclair Pharmaceuticals Limited, Surrey (GB)

( * ) Notice: Subject to any disclaimer, the term of this patent is extended or adjusted under 35 U.S.C. 154(b) by 202 days.

(21) Appl. No.: 12/161,593

(22) PCT Filed: Jan. 10, 2007

(86) PCT No.: PCT/GB2007/000053

§ 371 (c)(1),
(2), (4) Date: Sep. 18, 2008

(87) PCT Pub. No.: WO2007/091009

PCT Pub. Date: Aug. 16, 2007

(65) Prior Publication Data

US 2009/0036677 A1 Feb. 5, 2009

(30) Foreign Application Priority Data

Feb. 7, 2006 (GB) ................. 0602424.4

(51) Int. Cl.
*C07D 265/30* (2006.01)
*C07D 263/06* (2006.01)
(52) U.S. Cl. .............. 544/170; 548/215; 548/216
(58) Field of Classification Search .............. None
See application file for complete search history.

(56) References Cited

FOREIGN PATENT DOCUMENTS

DE 1 645 236 9/1970
EP 0 038 785 10/1981
WO WO 90/14342 11/1990

OTHER PUBLICATIONS

Vippagunta et al. Advanced Drug Delivery Reviews 48 (2001) pp. 3-26.*

* cited by examiner

*Primary Examiner*—Kamal A Saeed
*Assistant Examiner*—Nyeemah Grazier
(74) *Attorney, Agent, or Firm*—Saliwanchik, Lloyd & Eisenschenk

(57) ABSTRACT

It comprises a preparation process of delmopinol or a pharmaceutically acceptable salt and/or a solvate thereof, by submitting the compound of formula (II) where $R_1$ and $R_2$ are the same or different, independently selected from the group consisting of H, $(C_1\text{-}C_6)$-alkyl or, alternatively, $R_1$ and $R_2$ form, together with the carbon atom to which they are attached, a $(C_5\text{-}C_6)$-cycloalkyl radical; and $R_3$ is a radical selected from the group consisting of $CF_3$, $(C_1\text{-}C_4)$-alkyl, phenyl, and phenyl mono- or disubstituted by a radical selected from the group consisting of $(C_1\text{-}C_4)$-alkyl, halogen and nitro to a deprotection and cyclisation reaction. The process is useful to prepare delmopinol or its salts on an industrial scale. The compound of formula (II) is new and also forms part of the present invention, as well as its preparation process and other new intermediates of said preparation process.

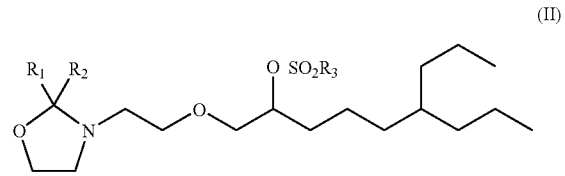

12 Claims, No Drawings

PREPARATION OF DELMOPINOL

This application is a National Stage Application of International Application Number PCT/GB2007/000053, filed Jan. 10, 2007; which claims priority to United Kingdom Application No. 0602424.4, filed Feb. 7, 2006, which are incorporated herein in their entirety.

FIELD OF THE INVENTION

The present invention relates to a process for the preparation of delmopinol, as well as to new intermediates useful in such a preparation process.

BACKGROUND ART

Delmopinol is the International Non-proprietary Name (INN) of 3-(4-propylheptyl)-4-morpholinethanol with CAS No. 79874-76-3. Delmopinol hydrochloride salt (CAS No 98092-92-3) is intended to be used in the treatment of gingivitis. The structure of delmopinol hydrochloride corresponds to the formula:

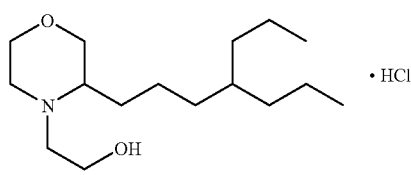

Different processes for the preparation of delmopinol and its salts are known in the art. EP 038785-A describes several preparation processes of this compound. According to EP038785-A, delmopinol can be prepared by alkylation of a 3-substituted morpholine, by dialkylation of a primary amine with a substituted bis(haloethyl)ether or a substituted diethyleneglycol disulfonate, by reduction of a morpholone, or by transformation of the N-substituent of the morpholine into a hydroxyethyl group. EP 0426826-A describes a process for the preparation of delmopinol which comprises a cycloaddition of a morpholine nitrone to obtain a morpholine-isoxazolidine or morpholine-isoxazoline, a reductive ring opening followed by transformation of functional groups present in the side chain, and finally alkylation of the nitrogen to yield delmopinol.

Despite the teaching of this prior art, research into new preparation processes of delmopinol is still an active field since the known processes are long and require the use of harsh hydrogenation conditions, some very toxic and/or flammable reagents or solvents which make their industrial exploitation difficult and expensive. Therefore, the provision of a new preparation process of delmopinol is highly desirable.

SUMMARY OF THE INVENTION

The inventors have found an efficient process for the preparation of delmopinol, as well as its pharmaceutically acceptable salts and/or solvates, which avoids the use of harsh hydrogenation conditions and extremely toxic and flammable reagents and solvents.

Thus, according to an aspect of the present invention, there is a process for the preparation of delmopinol of formula (I), or a pharmaceutically acceptable salt and/or a solvate thereof, including a hydrate,

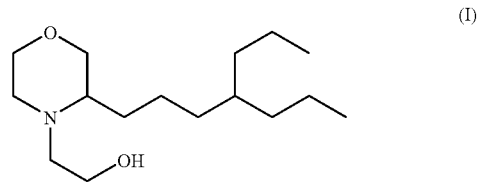

which comprises treating the compound of formula (II) either with a base in an appropriate solvent system, effecting both a deprotection of the amino ethanol and a cyclisation to yield the compound of formula (I) or, alternatively, treating the compound of formula (II) first with an acid in an appropriate solvent system at room temperature performing the deprotection of the amino ethanol, and then with a base effecting the cyclisation of the compound thus obtained to yield the compound of formula (I).

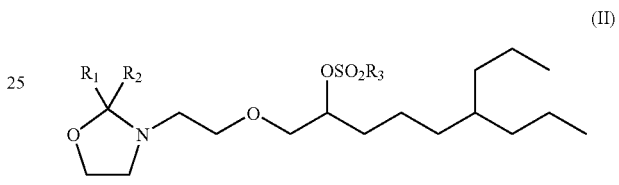

In the previous formula (II), $R_1$ and $R_2$ are a radical, same or different, independently selected from the group consisting of H, (C1-C6) alkyl or, alternatively, $R_1$ and $R_2$ form, together with the carbon atom to which they are attached, a (C5-C6) cycloalkyl radical; and $R_3$ is a radical selected from the group consisting of CF3, (C1-C4) alkyl, phenyl, and phenyl mono- or disubstituted by a radical selected from the group consisting of (C1-C4)-alkyl, halogen, and nitro.

The compound of formula (II) as defined above is previously prepared by reaction of a compound of formula (III) with a sulphonyl chloride of formula Cl—SO2-R3, where $R_1$, $R_2$, and $R_3$ have the same meaning defined above for the compound of formula (II).

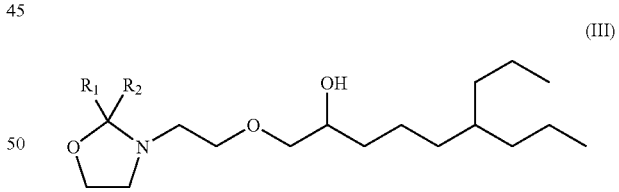

The compound of formula (III) is previously prepared by a process which comprises reacting a compound of formula (IV) where $R_1$ and $R_2$ have the meaning defined above, with a compound of formula (V) in the presence of a base, and recovering the compound of formula (III) obtained by treating the reaction mixture with a mixture of water and at least one water-immiscible solvent at approximately 0-5° C., followed by separating the organic phase, which contains the product, from the aqueous phase. The compound of formula (III), where $R_1$ is H and $R_2$ is a radical selected from the group consisting of H and (C1-C6) alkyl, can also be recovered in two steps through the formation of the compound of formula (VI) by treating the reaction mixture with an acid in the presence of water, followed by basification to isolate a compound of formula (VI) in neutral form. Subsequently, compound (VI) is subjected to a protection reaction characterised in that said compound (VI) is reacted with an aldehyde of formula R4CHO wherein R4 is selected from the group consisting of H and (C1-C6) alkyl to yield a compound of formula (III) wherein R1 is H and R2 is a radical selected from the group consisting of H and (C1-C6) alkyl.

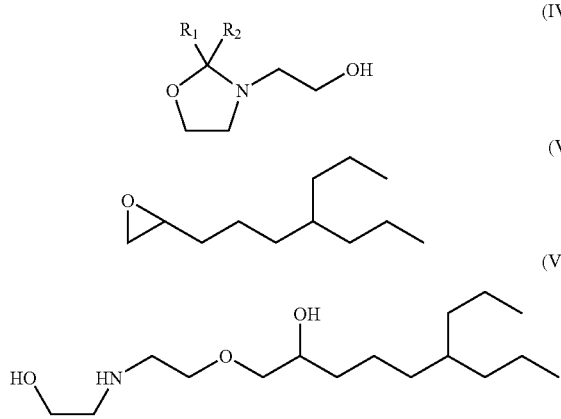

The compound of formula (V) is previously prepared by a process which comprises subjecting the compound of formula (VII) to an epoxidation reaction with an appropriate epoxidising agent.

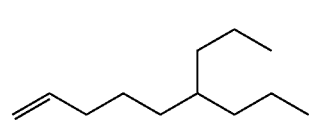

The compound of formula (VII) is previously prepared by subjecting the compound of formula (VIII) to an elimination reaction in the presence of an alkali metal alkoxide.

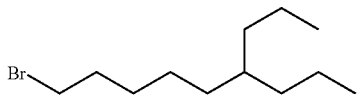

Among the advantageous features of the processes of the present invention, the following can be mentioned: the process uses cheap and non-toxic starting materials, the reagents and solvents used are also of low toxicity, the process is carried out under mild reaction conditions, yields of every reaction step are high, several steps of the process can be carried out in one pot, and delmopinol is obtained with high purity.

Compounds of formula (II), (III), (V), (VI), (VII) and (VIII) are new. Thus, another aspect of the present invention is the provision of said new intermediate compounds as defined above.

DETAILED DESCRIPTION OF THE INVENTION

As described above, delmopinol can be obtained by subjecting a compound of formula (II) as defined above to a deprotection and to a cyclisation reaction in an appropriate solvent system. In a preferred embodiment, the compound of formula (II) is that where R3 is methyl. Preferably, the solvent system is a mixture of a (C6-C8)-aromatic hydrocarbon and water. Examples of suitable hydrocarbons are toluene and xylene.

The transformation can be carried out by treating the compound of formula (II) with a base preferably at a temperature between 50° C. and reflux temperature of the biphasic solvent system employed. Alternatively, the process can be accelerated by treatment of the compound of formula (II) with a dilute acid such as hydrochloric acid at room temperature, thereby effecting the deprotection of the amino ethanol, followed by reaction with a base at a temperature preferably between 50° C. and reflux temperature of the solvent system employed, thereby effecting the cyclisation. The base in both cases can be either an inorganic base or an organic base, for example sodium hydroxide or triethylamine.

The most adequate conditions for carrying out said processes vary depending on the parameters considered by an expert in the art, such as, for example, the concentration of the reaction mixture, temperature, the solvent used, and the like. These can be readily determined by said skilled person in the art with routine tests and with the help of the teachings of the examples given in this description.

Delmopinol obtained by the process of the present invention may be converted into pharmaceutically acceptable salts, and salts may be converted into the neutral form, by standard procedures described in the art. For instance, delmopinol can be converted into its hydrochloride salt by treating delmopinol with hydrochloric acid in an appropriate solvent. Suitable solvents to carry out the crystallisation of the salt obtained are, for instance, (C2 C10)-ethers such as methyl tert-butyl ether or di-n-butyl ether, (C6-C8)-aliphatic hydrocarbons such as heptane or hexane, aromatic hydrocarbons such as toluene or xylene, and (C2 C10)-esters such as ethyl acetate, and mixtures thereof.

The compound of formula (II) can be previously prepared from the corresponding alcohol by reaction with a sulphonyl chloride of formula Cl—SO2-R3, where R3 has the same meaning as defined above. In a preferred embodiment, the sulfonyl chloride is that where R3 is —CH3, C6H4CH3, —C6H5 and —CF3. In a more preferred embodiment, R3 is methyl.

Generally, the reaction is carried out in the presence of a tertiary amine in an appropriate inert solvent such as a (C6-C8)-aromatic hydrocarbon such as toluene or xylene, or a chlorine-containing solvent such as methylene chloride or 1,2 dichloroethane, at a temperature between approximately 0° C. and room temperature.

Preferably, the reaction is carried out at low temperatures.

The preparation of the alcohol of formula (III) can be carried out by reacting a compound of formula (IV) as defined above with a compound of formula (V) in the presence of a base.

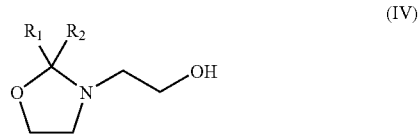

-continued

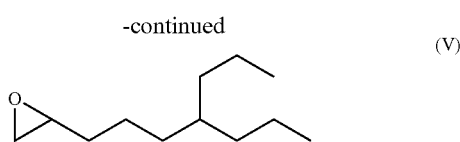
(V)

Preferably, the base is selected from the group consisting of an alkali metal alkoxide such as potassium tert-butoxide and an alkali metal hydride such as lithium hydride or sodium hydride. Generally, the reaction is carried out at a temperature between approximately 50° C. and 90° C.

Best results are obtained when the reaction is carried out using an excess of the compound of formula (IV). Preferably the molar ratio between (IV) and (V) is at least 4:1. More preferably, the molar ratio is at least 5:1 resulting in a yield of at least 90%.

The compound of formula (III) obtained can be isolated by treating the reaction mixture with a mixture of water and at least one water-immiscible solvent such as toluene at 0-5° C., followed by separating the organic phase containing the product from the aqueous phase.

The compound of formula (III) where R1 is H and R2 is a radical selected from H and (C1-C6) alkyl can also be isolated from the compound of formula (VI). After the reaction between compound (IV) and (V), the reaction mixture is treated with an acid in the presence of water, followed by addition of a base, yielding a compound of formula (VI) which is isolated in neutral form.

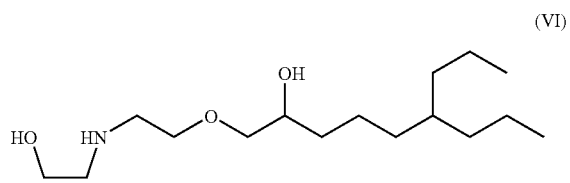
(VI)

After isolation, for instance by elimination of the solvent, compound (VI) is subjected to a protection reaction characterised in that said compound (VI) is reacted with an aldehyde of formula R4CHO where R4 is selected from H and (C1-C6)-alkyl. Preferably, the aldehyde is selected from formaldehyde and propionaldehyde.

It is possible to carry out two or more of the steps of the process in one pot, as is illustrated in the Examples. Thus, the reaction between the compounds of formula (IV) and (V) to give the compound of formula (III), followed by the work-up based on the treatment of the reaction mixture with a mixture of water and at least one water-immiscible solvent at 0-5° C., the subsequent conversion into the compound of formula (II) and the final formation of the compound of formula (I), can be carried out in one pot without isolation of any intermediate. Likewise, the conversion of the compound of formula (VI) into the compound of formula (III), the subsequent conversion into the compound of formula (II) and the final formation of the compound of formula (I) can also be performed in one pot, without isolation of any intermediate.

The compound of formula (IV) can be prepared from diethanolamine by means of a protection reaction. The process comprises the reaction of diethanolamine with an aldehyde or a ketone. Examples of suitable aldehydes are formaldehyde and propionaldehyde. Examples of suitable ketones are acetone, cyclopentanone, cyclohexanone, methyl isobutylketone, and methyl ethylketone.

The compound of formula (V) can be prepared by epoxidation of 6-propylnon-1-ene (VII) with an epoxidising agent such as 3-chloroperoxybenzoic acid or peroxyacetic acid. The compound of formula (VII) is previously prepared by submitting the corresponding alkyl bromide (VIII) to an elimination reaction in the presence of an alkali metal alkoxide, preferably potassium tert-butoxide. Said compound (VIII) is previously obtained by bromination of the corresponding alcohol (IX).

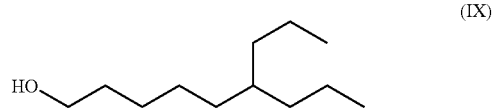
(IX)

The bromination can be carried out with a brominating agent in the presence of a suitable solvent. It can also be carried out, for instance, with hydrobromic acid and sulfuric acid without any solvent, preferably at reflux temperature. The 6-propylnonan-1-ol (IX) is known and can be prepared as described in Examples from methods known in the art.

Throughout the description and claims the word "comprise" and variations of the word, such as "comprising", are not intended to exclude other technical features, additives, components or steps. Additional objects, advantages and features of the invention will become apparent to those skilled in the art upon examination of the description or may be learned by practice of the invention.

The following examples are provided by way of illustration and are not intended to limit the scope of the present invention.

EXAMPLES

Example 1

Preparation of 6-propylnonane-1,6-diol

To a 250 mL two necked flask equipped with a condenser containing e-caprolactone (3.3 mL, 30 mmol) and anhydrous tetrahydrofuran (60 mL) under nitrogen atmosphere, was added at 0° C. dropwise propylmagnesium chloride (33 mL, 66 mmol, 2.2 eq., 2.0 M solution in diethyl ether). After addition, the reaction was stirred for 10 minutes at room temperature before heating to reflux for 2 hours. The reaction was monitored by thin layer chromatography. The reaction was cooled to 0° C. and saturated aqueous ammonium chloride (18 mL) was added followed, at room temperature, by hydrochloric acid (18 mL, 1M aqueous). The organic phase was decanted and the aqueous phase extracted with dichloromethane (3×140 mL). The combined organic phases were washed with saturated aqueous sodium bicarbonate (100 mL) before drying over magnesium sulfate. Evaporation of the solvent gave the title compound (6,543 g, 96%) as a viscous yellow oil. 1H NMR (CDCl3, 400 MHz) d?(ppm): 3.64 (t, J=6.7 Hz, 2H); 1.59 (tt, J=6.7 Hz, J=6.7 Hz, 2H); 1.46-1.24 (m, 15H); 0.88 (t, J=7.2 Hz, 6Hd). 13C NMR (CDCl3, 129.9 MHz) d?(ppm): 68.5; 64.2; 42.0 (2C'); 39.8; 33.1; 26.8; 23.7; 17.1 (2C'); 14.5 (2C'). MS (IC+) m/z (%): 220.2 [M+18] (99); 202.2 (75); 203.3 [M+1] (30); 185.2 (100); 176.2 (60); 141.2 (25).

Example 2

Preparation of 6-propylnon-5-en-1-ol and (Z)- and (E)-6-propylnon-6-en-1-ol

To a 100 mL flask equipped with a Dean-Stark collector containing 6-propylnonane-1,6-diol (94% purity, 6.5 g, 30 mmol) in solution with 60 mL toluene, was added para-toluenesulfonic acid (285 mg, 1.5 mmol, 0.05 eq) before heating to reflux. The reaction was monitored by thin layer chromatography. After 2 hours the reaction is cooled to room temperature 160 mL toluene was added and the organic phase was washed with sodium bicarbonate (½ sat. aq., 3×15 mL). The organic phase was dried with magnesium sulfate and evaporation gave of a mixture of the three title isomers (5.43 g, 98% yield) as a pale yellow oil. 1H NMR (CDCl3, 400 MHz) d?(ppm): 5.14-5.08 (m, 3H); 3.67-3.61 (m, 6H); 2.07-1.90 (m, 18H); 1.64-1.53 (m, 6H); 1.46-1.31 (m, 21H); 0.94 (t, J=7.4 Hz, 3H'); 0.93 (t, J=7.4 Hz, 3H); 0.88 (t, J=7.4 Hz, 6H); 0.87 (t, J=7.4 Hz, 3H); 0.86 (t, J=7.4 Hz, 3H'). 13C NMR (CDCl3, 129.9 MHz) d?(ppm): 139.6; 138.5 (2C); 126.8; 126.7; 63.0; 39.0; 36.8; 32.8; 32.7; 32.5; 32.1; 32.0; 29.9; 28.3; 28.0; 27.4; 26.2; 25.8; 25.5; 21.7; 21.6; 21.3; 21.0; 14.7; 14.2; 13.9. MS (IC+) m/z (%): 202.3 [M+18] (80); 185.3 [M+1] (100); 104.1 (59); 77.1 (50).

Example 3

Preparation of 6-propylnonan-1-ol

To a 100 mL flask containing a mixture of the three isomers obtained in Example 2 (5.43 g, 29.5 mmol) and absolute ethanol (70 mL) under nitrogen atmosphere, was added Pd/C 10% (543 mg, 10% mass). The vessel was purged with nitrogen followed by hydrogen with good stirring. The flask was equipped with a balloon containing hydrogen and the reaction was stirred at room temperature for 24 h. The reaction was monitored by 1H NMR. The reaction was purged with nitrogen and the catalyst was filtered off with a filter funnel (no 3) containing Celite® and washed several times with absolute ethanol. Evaporation gave 6-propylnonan-1-ol (4.92 g, 90% yield) as a colorless oil. 1H NMR (CDCl3, 400 MHz) d?(ppm): 3.64 (t, J=6.7 Hz, 2H); 1.58 (tt, J=6.7 Hz, J=6.7 Hz, 2H); 1.39-1.14 (m, 15H); 0.88 (t, J=6.8 Hz, 6H). 13C NMR (CDCl3, 129.9 MHz) d?(ppm): 63.0; 36.9; 36.0 (2C'); 33.6; 32.8; 26.5; 26.2; 19.8 (2C); 14.5 (2C).

Example 4

Preparation of 1-bromo-6-propylnonane

To a 50 mL flask containing 6-propylnonan-1-ol (4.92 g, 26.4 mmol) was added hydrobromic acid 48% (12 mL, 105.6 mmol, 4 eq.) and conc. sulfuric acid (1.4 mL, 26.4 mmol, 1 eq.) and the mixture was heated to reflux (95° C.) for 14 h. The reaction was cooled to room temperature before adding H2O (40 mL). The mixture was extracted with dichloromethane (3×120 mL) and the combined organic phases were washed with aqueous sodium bicarbonate (40 mL, 1M). Drying over magnesium sulfate and evaporation gave 1-bromo-6-propylnonane (5.87 g, 89% yield) as a brown liquid. 1H NMR (CDCl3, 400 MHz) d?(ppm): 3.40 (t, J=6.8 Hz, 2H); 1.86 (tt, J=6.8 Hz, J=6.8 Hz, 2H); 1.45-1.35 (m, 2H); 1.34-1.15 (m, 13H); 0.88 (t, J=6.8 Hz, 6H). 13C NMR (CDCl3, 129.9 MHz) d?(ppm): 36.9; 36.0 (2C); 34.0; 33.5; 33.9; 28.7; 25.8; 19.8 (2C); 14.5 (2C).

Example 5

Preparation of 6-propylnon-1-ene

To a 250 mL flask containing potassium tert-butoxide (13.27 g, 108.7 mmol, 4.6 eq.) under nitrogen atmosphere was added anhydrous tetrahydrofuran (100 mL) and via cannula 1-bromo-6-propylnonane (5.87 g, 23.54 mmol) in solution with anhydrous tetrahydrofuran (20 mL) was transferred at 0° C. The mixture was then stirred at room temperature for 2 h. Hydrochloric acid (230 mL, 1M) was added slowly and the mixture was extracted with cyclohexane (300 mL+3×100 mL). The combined organic phase was washed with aqueous sodium bicarbonate (100 mL, 1M) and dried over magnesium sulfate. The solvent was carefully evaporated under moderate vacuum (at room temperature because of the high volatility of the alkene) to give 3.3 g (84%) of 6-propylnon-1-ene as a brown liquid. 1H NMR (CDCl3, 400 MHz) d?(ppm): 5.82 (ddt, J=6.8 Hz, J=10.2 Hz, J=16.9 Hz, H); 5.00 (broad d, J=16.9 Hz, H); 4.93 (broad d, J=10.2 Hz, H); 2.02 (dt, J=6.8 Hz, J=6.8 Hz, 2H); 1.41-1.30 (m, 2H); 1.32-1.15 (m, 11H); 0.88 (t, J=7.1 Hz, 6H'). 13C NMR (CDCl3, 129.9 MHz) d?(ppm): 139.3; 114.1; 36.8; 36.1 (2C); 34.3; 33.2; 26.0; 19.8 (2C); 14.5 (2C). MS (IE) m/z (%) 169.1 [M+] (25); 141.1 (30); 125.0 (57); 113.0 (40); 99.0 (44); 85.0 (67); 71.0 (73).

Example 6

Preparation of 2-(4-propyl-heptyl)-oxirane

To a 250 ml flask containing 6-propylnon-1-ene (4 g, 23.76 mmol, purified by distillation) and anhydrous dichloromethane (260 mL) under nitrogen atmosphere, was added at 0° C. meta-chloroperoxybenzoic acid (77%, 10.65 g, 47.53 mmol, 2 eq) and the reaction was stirred for 20 minutes at 0° C. before warming to room temperature. The disappearance of starting material is monitored by TLC. The reaction was evaporated almost to dryness and cyclohexane (260 ml) was added and the remaining solid in the flask was extracted several times with cyclohexane. The combined organic phases were then washed with saturated aqueous sodium bicarbonate (5×25 mL). After evaporation of the solvent, the crude was purified by column chromatography (eluent dichloromethane) to give the desired product (3.86 g, 88%) as a colourless oil.

To a solution of 6-propylnon-1-ene (16.35 g, 97.34 mmol) in toluene (90 ml) and aqueous sodium acetate (4.87 ml, 1 M, 4.87 mmol) at ambient temperature was added peroxyacetic acid (24.55 ml, 32 wt % in dilute acetic acid, 116.81 mmol) dropwise over 10 min. The mixture was heated to 60° C. and the reaction progress followed by gas chromatography (GC). After 5 h, GC indicated 3% remaining alkene and the mixture was left stirring at ambient temperature for 16 h, after which only 1% alkene remained (85.7% overall purity, containing 8.7% saturated hydrocarbon contaminant from alkene). On completion, the biphasic mixture was treated with aqueous sodium bisulfite (10%, 80 ml) and the organic phase was separated. The aqueous phase was extracted with toluene (2×40 ml) and the combined organic phases were washed with water (2×40 ml), dried over sodium sulfate, filtered and concentrated in vacuo to give a pale yellow oil (20.9 g, 117%). Purification by chromatography (silica, dichloromethane) gave 2-(4-propyl-heptyl)-oxirane (14.42 g, 81%) as a colourless oil. 0.42 Eluent (CH2Cl2); Rev.: Anisaldehyde; Colour: blue-green. 1H NMR (CDCl3, 400 MHz) d?(ppm): 2.94-2.87 (m, H); 2.74 (dd, J=3.9 Hz, J=4.9 Hz, H); 2.46 (dd, J=2.7 Hz, J=4.9 Hz, H); 1.55-1.47 (m, 2H); 1.49-1.36 (m, 2H); 1.36-1.17 (m, 11H); 0.88 (t, J=6.8 Hz, 6H). 13C NMR (CDCl3, 129.9 MHz) d??(ppm): 52.4; 47.1; 36.9; 35.9 (2C); 33.4; 32.9; 23.1; 19.8 (2C); 14.5 (2C).

Example 7

Preparation of 2,2-dimethyl-3-(2-hydroxyethyl)-oxazolidine

To a 100 mL flask containing diethanolamine (19.2 mL, 200 mmol) was added acetone (29.4 mL, 400 mmol, 2 eq.) and potassium carbonate (pulverised and dried at 160° C., 27.6 g, 200 mmol, 1 eq.). The reaction was stirred at room temperature for one day. The mixture was filtered through a sinter funnel (no. 3) and the collected solid was washed with acetone. The filtrate and the washes were combined and the solvent evaporated. The 1H NMR indicated a conversion of 85%. Distillation at 125-132° C./20 mmHg of the crude reaction gave the title product (20.89 g, 72% yield) as a colourless oil. 1H NMR (CDCl3, 400 MHz) d?(ppm): 3.93 (t, J=6.6 Hz, 2H); 3.62 (t, J=5.3 Hz, 2H); 2.96 (t, J=6.6 Hz, 2H); 2.65 (t, J=5.3 Hz, 2H); 1.23 (s, 6H). 13C NMR (CDCl3, 129.9 MHz) d??(ppm): 94.2; 63.5; 59.3; 50.8; 49.1; 23.3 (2C).

Example 8

Preparation of 2-(1-oxa-4-aza-spiro[4,5]dec-4-yl)-ethanol

To a 50 mL flask containing diethanolamine (9.7 mL, 100 mmol) was added cyclohexanone (10.4 mL, 100 mmol, 1 eq.) and potassium carbonate (pulverized and dried at 160° C., 13.8 g, 100 mmol, 1 eq.). The reaction was stirred at 80° C. for 12 h. The reaction was cooled to room temperature and diluted with dichloromethane before filtering off potassium carbonate. The crude mixture diluted in cyclohexane was washed with water at 0° C. Drying with sodium sulfate and evaporation afforded the title product (8.4 g, 45% yield). 1H NMR (CDCl3, 400 MHz) d?(ppm): 3.91 (t, J=6.7 Hz, 2H); 3.60 (m, 2H); 3.00 (t, J=6.7 Hz, 2H); 2.70 (t, J=5.3 Hz, 2H); 1.72-1.50 (m, 7H); 1.43-1.30 (m, 2H); 1.21-1.04 (m, 1H). 13C NMR (CDCl3, 129.9 MHz) d?(ppm): 94.9; 63.2; 59.2; 50.3; 49.0; 32.6 (2C); 25.6; 23.3 (2C).

Example 9

Preparation of 2-oxazolidin-3-yl-ethanol

To a 250 mL flask containing paraformaldehyde (11.41 g, 380 mmol, 1 eq.) in toluene (76 mL), was added diethanolamine (36.5 mL, 380 mmol d=1.0955) diluted with isopropanol (76 mL) before heating to reflux with a Dean-Stark trap for 19 h. The reaction was cooled to room temperature and, after evaporation, 47.57 g of crude product was obtained. The crude obtained was purified by distillation with vacuum to give the title compound (38.33 g, 86% yield). 1H NMR (CDCl3, 400 MHz) d?(ppm): 4.32 (s, 2H); 3.78 (t, J=6.7 Hz, 2H); 3.64 (t, J=5.3 Hz, 2H); 3.00 (t, J=6.7 Hz, 2H); 2.73 (t, J=5.3 Hz, 2H).

Example 10

Preparation of 2-(2-ethyl-oxazolidin-3-yl)-ethanol

To a 250 mL flask containing diethanolamine (2.9 mL, 30 mmol d=1.0955) in dichloromethane (60 mL) under nitrogen atmosphere, was added potassium carbonate (8.3 g, 60 mmol, 2 eq.) before adding at 0° C. dropwise propionaldehyde (2.73 mL, 37.5 mmol, 1.25 eq.). The reaction was warmed to room temperature and stirred for 3 h. The potassium carbonate was filtered with a sinter funnel and washed several times with dichloromethane. After evaporation of the combined organic phases, 4.994 g of crude product was obtained. The product was purified by distillation under vacuum to give the title compound (3.87 g, 87% yield). 1H NMR (CDCl3, 400 MHz) d?(ppm): 3.93 (dd, J=4.3 Hz, J=6.4 Hz, H); 3.92-3.82 (m, 2H); 3.71-3.58 (m, 2H); 3.26 (ddd, J=5.5 Hz, J=6.5 Hz, J=12.2 Hz, H); 2.83 (ddd, J=4.9 Hz, J=8.2 Hz, J=12.7 Hz, H); 2.66 (dt, J=7.0 Hz, J=110.0 Hz, H); 2.55 (dt, J=3.9 Hz, J=12.2 Hz, H); 1.60 (ddq, J=4.3 Hz, J=7.4 Hz, J=14.1 Hz); 1.51 (ddq, J=6.4 Hz, J=7.4 Hz, J=14.1 Hz); 0.95 (t, J=7.4 Hz, 3H). 13C NMR (CDCl3, 129.9 MHz) d?(ppm): 97.5; 64.1; 60.0; 55.1; 51.7; 26.8; 8.9.

Example 11

Preparation of 1-[2-(2-hydroxy-ethylamino)-ethoxy]-6-propyl-nonan-2-ol

To a 10 mL Schlenk tube containing potassium tert-butoxide (125 mg, 1 mmol, 0.5 eq.) under nitrogen atmosphere, was added freshly distilled 2,2-dimethyl-3-(2-hydroxyethyl)-oxazolidine (1.4 mL, 10 mmol, d 1.035, 5 eq.) before heating at 75° C. until complete dissolution. To the solution was added slowly 2-(4-propyl-heptyl)-oxirane (0.43 mL, 2 mmol, d 0.856) over 1 h at 75° C. The reaction was stirred at 75° C. After 6 h, the reaction was cooled to room temperature before adding diethyl ether (40 mL). The organic phase was extracted with aqueous hydrochloric acid (1M, 3×12 mL). Then, a solution of aqueous sodium hydroxide (25%) was added to bring the mixture to pH 14 before extracting it with diethyl ether (4×16 mL). The combined organic phases were dried over sodium sulfate and concentrated to afford the title compound (515 mg, 90% yield). 1H NMR (CDCl3, 400 MHz) d?(ppm): 3.83-3.74 (m, H); 3.67 (t, J=5.2 Hz, 2H); 3.67-3.56 (m, 2H); 3.52 (dd, J=2.7 Hz, J=9.9 Hz, H); 3.30 (dd, J=8.2 Hz, J=9.9 Hz, H); 3.05-2.96 (m, 2H+2H); 1.50-1.15 (m, 15H); 0.87 (t, J=7.0 Hz, 6H). 13C NMR (CDCl3, 129.9 MHz) d?(ppm): 75.9; 70.3; 70.2; 60.9; 51.1; 48.9; 36.9; 36.0 (2C); 33.7; 33.6; 22.7; 19.8 (2C); 14.5 (2C).

Example 12

Preparation of 1-[2-(2,2-dimethyl-oxazolidin-3-yl)-ethoxy]-6-propyl)-nonan-2-ol To a 250 mL flask containing sodium methoxide (1.35 g 25 mmol, 0.25 eq) under nitrogen atmosphere, was added freshly distilled 2,2-dimethyl-3-(2-hydroxyethyl)-oxazolidine (70.15 mL 500 mmol, d 1.035, 5 eq.) before heating at 50° C. until complete dissolution (20 min). The reaction was then connected to a vacuum line (3-4 mBar) for 90 min to remove the methanol formed in situ. To the solution was added slowly 2-(4-propyl-heptyl)-oxirane (21.53 mL 100 mmol, d 0.856) over 1 h at 75° C. The reaction was stirred overnight at 75° C. After 17 h, the reaction was cooled to room temperature before adding toluene (125 mL). To the mixture cooled to 0° C. was added water (100 mL, precooled to 0 oC) before stirring for 1 h at 0° C. The organic phase was recovered and the aqueous phase was extracted with toluene (2×35 mL, precooled to 0° C.). The combined organic phases were washed with 25 mL water (precooled to 0° C.) and partially evaporated (by 15% vol.) at 35° C. with vacuum (30 mBar) to effect azeotropic drying. The organic phase was diluted with toluene (32 mL) and was used directly in the next step. It was possible to isolate the product by evaporating the solvent on a rotavapor. 1H NMR (CDCl3, 400 MHz) d?(ppm): 3.91 (t, J=6.6 Hz, 2H); 3.81-3.73 (m, H); 3.67 (dt, J=5.6 Hz, J=10.2 Hz, H); 3.61 (dt, J=5.6 Hz, J=10.2 Hz, H); 3.56 (dd, J=2.7 Hz, J=10.2 Hz, H); 3.30 (dd, J=8.2 Hz, J=10.2 Hz, H); 3.05-2.96 (m, 2H); 2.67 (t, J=5.6 Hz, 2H4); 1.50-1.15 (m, 21H); 0.87 (t, J=7.0 Hz, 6H). 13C NMR (CDCl3, 129.9 MHz) d?(ppm): 94.5; 76.0; 70.7; 70.5; 63.5; 50.4; 49.5; 36.9; 36.0 (2C); 33.7; 33.5; 23.1; 23.0; 22.7; 19.7 (2C); 14.5 (2C).

Example 13

Preparation of 1-(2-oxazolidin-3-yl-ethoxy)-6-propyl-nonan-2-ol

To a 10 mL flask containing paraformaldehyde (52 mg, 1.73 mmol, 1 eq.) in toluene (1 mL), was added 1-[2-(2-hydroxy-ethylamino)-ethoxy]-6-propyl-nonan-2-ol (500 mg 1.73 mmol) diluted with isopropanol (1 mL) before heating to reflux with a Dean-Stark trap for 17 h. The reaction was cooled to room temperature and, after evaporation, 520 mg of a mixture of products was obtained with the title compound as the major component (100% crude yield). 1H NMR (CDCl3, 400 MHz) d?(ppm): 4.33 (s, 2H); 3.78 (t, J=6.8 Hz, 2H); 3.83-3.74 (m, H); 3.70-3.57 (m, 2H); 3.55 (dd, J=2.7 Hz, J=10.0 Hz, H); 3.29 (dd, J=8.2 Hz, J=10.0 Hz, H); 3.02 (t, J=6.8 Hz, 2H); 2.81-2.74 (m, 2H); 1.50-1.12 (m, 15H); 0.87 (t, J=7.0 Hz, 6H'). 13C NMR (CDCl3, 129.9 MHz) d?(ppm): 87.0; 76.0; 70.5; 70.3; 63.3; 54.3; 52.7; 36.9; 36.0 (2C); 33.7; 33.5; 22.7; 19.8 (2C); 14.5 (2C)

Example 14

Preparation of 1-[2-(2-ethyl-oxazolidin-3-yl)-ethoxy]-6-propyl-nonan-2-ol

To a 10 mL flask containing 1-[2-(2-hydroxy-ethylamino)-ethoxy]-6-propyl-nonan-2-ol (510 mg, 1.76 mmol, 1 eq.) in toluene (3 mL) was added dropwise at room temperature propionaldehyde (0.14 mL 1.85 mmol, 1.05 eq., d=0.798) before heating to reflux with a Dean-Stark trap for 2 h. The reaction was cooled to room temperature and concentrated to afford the title compound as 2 stereoisomers (50:50) (580 mg, 100% yield). 1H NMR (CDCl3, 400 MHz) d?(ppm): 4.09-4.03 (m, H); 3.92-3.81 (m, 2H); 3.81-3.73 (m, H); 3.73-3.50 (m, 2H+2H); 3.35-3.21 (m, 2H); 2.92-2.74 (m, 2H); 2.72-2.63 (m, H); 2.62-2.52 (m, H); 1.69-1.14 (m, 15H+2H); 0.96 (m, 3H); 0.87 (t, J=7.0 Hz, 6H). 13C NMR (CDCl3, 129.9 MHz) d?(ppm): 98.0; 97.9; 76.1; 75.7; 70.6 (2C); 70.2 (2C); 64.2 (2C); 53.2; 53.1; 52.6 (2C); 36.9 (2C); 36.0 (2C+2C); 33.7 (2C); 33.6; 33.5; 26.9; 26.8; 22.7 (2C); 19.8 (2C+2C); 14.5 (2C+2C); 9.2 (2C).

Example 15

Preparation of methanesulfonic acid 1-[2-(2,2-dimethyl-oxazolidin-3-yl)-ethoxymethyl]-5-propyl)-octyl ester To a 500 mL flask containing the crude solution of 1-[2-(2,2-dimethyl-oxazolidin-3-yl)-ethoxy]-6-propyl)-nonan-2-ol was added at 0° C. triethylamine (distilled over calcium hydride and stored over molecular sieves 3 Å, 33.6 mL, 240 mmol, 2.4 eq.) and methanesulfonyl chloride (9.29 mL 120 mmol, 1.2 eq.). The reaction was stirred at 0° C. and monitored by TLC. After 90 min, TLC indicated complete conversion and the reaction mixture was directly used for the next step.

The isolation of the title compound (1.8 mmol scale) could be carried out by evaporating the solvent, diluting the residue with dichloromethane (15 mL), and washing the organic phase with water (3×3 mL) followed by saturated aqueous sodium chloride (4 mL). Drying over sodium sulfate and evaporation furnished the title compound (586 mg, 80% Yield). 1H NMR (CDCl3, 400 MHz) d?(ppm): 4.83-4.76 (m, H7); 3.89 (t, J=6.8 Hz, 2H); 3.69-3.52 (m, 2H+2H); 3.09 (s, 3H); 3.04-2.94 (m, 2H); 2.70-2.60 (m, 2H); 1.72-1.54 (m, 2H); 1.47-1.10 (m, 19H); 0.88 (t, J=6.8 Hz, 6H). 13C NMR (CDCl3, 129.9 MHz) d?(ppm): 94.7; 82.7; 72.9; 71.2; 63.8; 50.7; 49.1; 38.9; 37.0; 36.1 (2C); 33.7; 32.4; 23.4; 23.1; 22.4; 19.9 (2C); 14.7 (2C).

Example 16

Preparation of methanesulfonic acid 1-[2-(2-ethyl-oxazolidin-3-yl)-ethoxymethyl]-5-propyl-octyl ester To a 10 mL flask containing the crude solution of 1-[2-(2-ethyl-oxazolidin-3-yl)-ethoxy]-6-propyl-nonan-2-ol (1.71 mmol) in toluene (3.5 mL) was added at 0° C. triethylamine (distilled over CaH2 and stored over molecular sieves 3 Å, 575 µL, 4.1 mmol, 2.4 eq.) and methanesulfonyl chloride (158 µL, 2 mmol, 1.2 eq.). The reaction was stirred at 0° C. and monitored by TLC. After 60 min, TLC indicated complete conversion and the reaction mixture was directly used for the next step.

The isolation of the title compound was carried out by evaporating the solvent, diluting the residue with dichloromethane (15 mL), and washing the organic phase with water (3×3 mL) followed by saturated aqueous sodium chloride (4 mL). Drying over sodium sulfate and evaporation furnished the title compound as 2 stereoisomers (524 mg, 75% yield). 1H NMR (CDCl3, 400 MHz) d?(ppm): 4.83-4.73 (m, 2×H); 4.06-3.96 (m, 2×H); 3.90-3.80 (dd, J=5.9 Hz, J=7.2 Hz, 2×2H); 3.70-3.54 (m, 2×2H5+2×2H); 3.31-3.22 (m, 2H); 3.08 (s, 2×3H); 2.88-2.77 (m, 2H); 2.70-2.59 (m, 2H); 2.59-2.48 (m, 2H); 1.74-1.52 (m, 2×2H8); 1.52-1.14 (m, 2×15H); 0.94 (t, J=7.4 Hz, 2×3H); 0.88 (t, J=6.8 Hz, 2×6H). 13C NMR (CDCl3, 129.9 MHz) d?(ppm): 94.80; 94.75; 82.38; 82.29; 72.6 (2C); 70.7 (2C); 64.23; 64.19; 52.71; 52.66; 52.58;

52.57; 38.55; 38.54; 36.7 (2C); 35.84 (2C'); 35.82 (2C); 33.4 (2C); 32.1 (2C); 26.81; 26.77; 22.1 (2C); 19.7 (4C); 14.4 (4C); 9.05; 9.03.

Example 17

Preparation of Delmopinol

To a 500 mL flask containing the crude mesylation reaction obtained in Example 15, was added deionised water (65 mL) before heating to reflux (approx. 95° C.). After 17 h, the reaction was cooled to room temperature and the aqueous phase was separated from the organic phase. The aqueous phase was extracted with toluene (25 mL). The combined organic phases were evaporated to a volume of 200 mL (approx. 5 vol.) before adding water (120 mL). To the well stirred mixture, was added sufficient concentrated sulfuric acid to bring the mixture to pH 1. The two phases were separated and the aqueous phase was washed with toluene (2×20 mL). An organic solvent (120 mL of toluene, xylene or di-n-butyl ether) was added to the aqueous phase, followed, with good stirring, by a solution of aqueous sodium hydroxide (25%) to bring the mixture to pH 14. The mixture was heated at 60° C. for 10 min before separating the phases. The aqueous phase was extracted with 20 mL of the corresponding organic solvent using the same procedure as before (60° C. for 10 min before separating the phases). The combined organic phases were washed with aqueous ammonia (0.5%, 2×15 mL). After each wash, the mixture was heated to 60° C. for 10 min. The organic phase was half evaporated to remove traces of ammonia. Active carbon (5 wt %, Norit SX Plus) was added, and the mixture was heated to 50° C. for 20 min. The active carbon was filtered off and the solvent was evaporated to give crude delmopinol (24 g, 89% crude yield) as a yellow oil.

Example 18

Preparation of Delmopinol

To a 25 mL flask containing the crude mesylation reaction obtained in Example 16 (1.78 mmol product), was added deionised water (3.5 mL) before heating to reflux (approx. 95° C.). After 17 h, the reaction was cooled to room temperature and the aqueous phase was separated from the organic phase. The aqueous phase was extracted twice with toluene (2×7 mL). The combined organic phases were washed with aqueous sodium chloride (3×9 mL, 20% saturated). After drying over sodium sulfate the purification was carried out by column chromatography (eluent methanol/dichloromethane: 0/100 to 5/95) to furnish delmopinol (337 mg, 70% yield). 1H NMR (CDCl3, 400 MHz) d?(ppm): 3.79-3.70 (m, 2H); 3.69-3.60 (m, 2H); 3.59 (m, 1H); 3.45 (dd, J=7.0 Hz, J=11.3 Hz, H); 2.98-2.89 (m, 1H); 2.88-2.78 (m, 1H); 2.45-2.30 (m, 3H); 1.56-1.36 (m, 2H); 1.36-1.11 (m, 13H); 0.88 (t, J=7.0 Hz, 6H). 13C NMR (CDCl3, 400 MHz) d?(ppm): 70.5; 67.1; 59.8; 57.8; 54.6; 49.8; 36.9; 36.0 (C); 35.9 (C); 34.0; 27.3; 23.3; 19.8 (C); 19.7 (C); 14.5 (2C).

Example 19

Preparation of Delmopinol Hydrochloride

To a 25 mL flask containing the crude delmopinol in solution with toluene or xylene coming from the last work-up, was added hydrochloric acid (37%, 1 eq.) before distilling a part of the solvent to eliminate the water. Toluene or xylene was added at 60° C. to obtain a homogeneous organic phase (to obtain 4 mL/g delmopinol in total). Then, heptane (5 mL/g delmopinol) or di-n-butyl ether (4 mL/g delmopinol) was added before cooling the mixture to room temperature. After seeding, the mixture was stirred 1 h at room temperature and 3 h at 0° C. The solid was filtered with a sinter funnel and washed at 0° C. with the same solution used for the crystallisation (1 mL/g delmopinol). Drying under vacuum gave delmopinol hydrochloride (50-70% yield) as a white powder.

Example 20

Preparation of Delmopinol Hydrochloride

To a 25 mL flask containing 2 g crude delmopinol in solution with toluene, xylene or dibutyl ether coming from the last work-up, was added hydrochloric acid (37%, 1 eq.) before distilling partially or to dryness (if toluene or xylene) to eliminate water. Di-n-butyl ether (to obtain 5 mL/g delmopinol in total) was added to delmopinol hydrochloride before heating at 60° C. Then a polar solvent (ethyl acetate 1.3 mL/g delmopinol) was added dropwise to the solution to effect complete dissolution, and the mixture was cooled to room temperature before seeding and stirring 1 h at room temperature and 2 h at 0° C. The solid was filtered with a sinter funnel and was washed at 0° C. with the same solution used for the crystallisation (1 mL/g delmopinol). Drying under vacuum gave delmopinol hydrochloride (1.51 g, 67% yield, 60% overall yield from (V)) as a white powder. 1H NMR (CDCl3, 400 MHz) d??(ppm): 11.98-11.69 (m, 1H); 4.42-4.29 (m, 1.3H); 4.14-3.91 (m, 4.5H); 3.89-3.73 (m, 1.3H); 3.64-3.55 (m, 1H); 3.48-3.37 (m, 1H); 3.24-2.89 (m, 3H); 2.01-1.78 (m, 2H); 1.61-1.12 (m, 13H); 0.88 (t, J=7.0 Hz, 6H). 13C NMR (CDCl3, 400 MHz) d?(ppm): 67.7 (C—O); 65.1 (C—N min.); 63.6 (C—O); 63.2 (C maj.); 59.9 (C min.); 57.1 (C—N maj.); 55.9 (C); 53.2 (C—N maj.); 48.3 (C—N min.); 36.6 (C); 35.6 (C); 35.5 (C); 33.3; 27.1; 22.9; 19.5 (2C'); 14.3 (2C)

The invention claimed is:

1. A process for the preparation of delmopinol of formula (I) or a pharmaceutically acceptable salt and/or a solvate thereof,

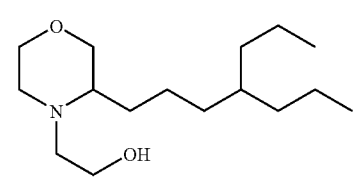

(I)

which comprises treating the compound of formula (II)

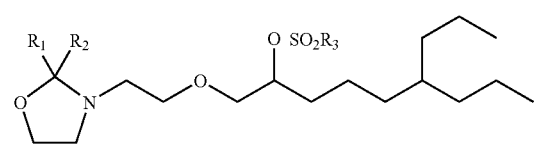

(II)

wherein:

$R_1$ and $R_2$ are a radical, same or different, independently selected from the group consisting of H, (C1-C6) alkyl or, alternatively, $R_1$ and $R_2$ form, together with the carbon atom to which they are attached, a (C5-C6) cycloalkyl radical; and $R_3$ is a radical selected from the group consisting of $CF_3$, (C1-C4) alkyl, phenyl, and phenyl mono- or disubstituted by a radical selected from the group consisting of (C1-C4)-alkyl, halogen and nitro;

either with a base in an appropriate solvent system performing both a deprotection of the amino ethanol and a cyclisation to yield the compound of formula (I) or, alternatively, first with an acid in an appropriate solvent system at room temperature performing the deprotection of the amino ethanol, and then with a base performing the cyclisation of the compound obtained to yield the compound of formula (I).

2. The process according to claim 1, wherein the solvent system is a mixture of a (C6-C8)-aromatic hydrocarbon and water.

3. The process according to claim 1, wherein the compound of formula (II) is prepared by reaction of a compound of formula (III) with a sulphonyl chloride of formula $Cl-SO_2-R_3$, wherein $R_1$ and $R_2$ are a radical, same or different, independently selected from the group consisting of H, (C1-C6) alkyl or, alternatively, $R_1$ and $R_2$ form, together with the carbon atom to which they are attached, a (C5-C6) cycloalkyl radical; and $R_3$ is a radical selected from the group consisting of $CF_3$, (C1-C4) alkyl, phenyl, and phenyl mono- or disubstituted by a radical selected from the group consisting of (C1-C4)-alkyl, halogen and nitro (III)

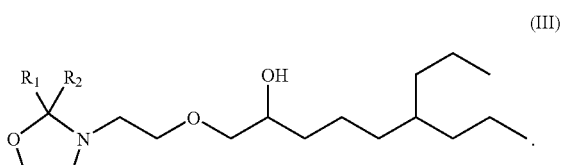

4. The process according to claim 3, wherein the compound of formula (III) is prepared by a process which comprises reacting a compound of formula (IV) wherein $R_1$ and $R_2$ have the meaning defined in claim 1 for compound (II), with a compound of formula (V) in the presence of a base (IV)

(V)

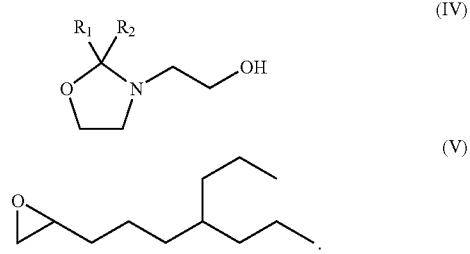

5. The process according to claim 4, wherein the molar ratio between (IV) and (V) is at least 4:1.

6. The process according to claim 4, wherein the base is selected from an alkali metal alkoxide and an alkali metal hydride.

7. The process according to claim 4, further comprising recovering the compound of formula (III) by treating the reaction mixture with a mixture of water and at least one water-immiscible solvent at 0-5° C., followed by separating the organic phase containing the product from the aqueous phase.

8. The process according to claim 4, further comprising treating the reaction mixture with an acid in the presence of water, followed by basification to a pH of approximately 9-11 to isolate a compound of formula (VI) in neutral form, (VI)

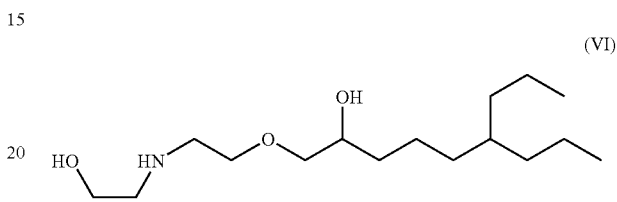

and then submitting the compound (VI) obtained to a protection reaction characterised in that said compound (VI) is reacted with an aldehyde of formula R4CHO wherein R4 is selected from the group consisting of H and (C1-C6) alkyl to yield a compound of formula (III) wherein $R_1$ is H and $R_2$ is a radical selected from the group consisting of H and (C1-C6) alkyl.

9. The process according to claim 4, wherein the compound of formula (V) is prepared by submitting the compound of formula (VII) to an epoxidation reaction with an appropriate epoxidising agent (VII)

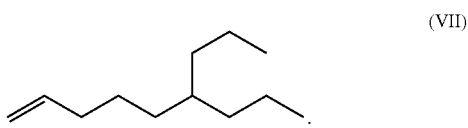

10. The process according to claim 9, wherein the epoxidising agent is selected from the group consisting of meta-chloroperoxybenzoic acid and peroxyacetic acid.

11. The process according to claim 9, wherein the compound of formula (VII) is prepared by submitting the compound of formula (VIII) to an elimination reaction in the presence of an alkali metal alkoxide (VIII)

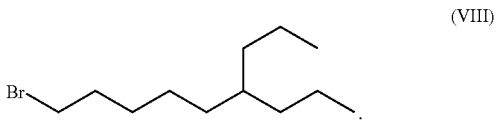

12. The process, according to claim 1, wherein the solvate is a hydrate.

* * * * *